United States Patent [19]

Drent

[11] Patent Number: 4,849,542
[45] Date of Patent: Jul. 18, 1989

[54] PROCESS FOR THE PREPARATION OF OXO-ALKANEDIOIC ACIDS OR DIESTERS THEREOF

[75] Inventor: Eit Drent, CM Amsterdam, Netherlands

[73] Assignee: Shell Oil Company, Houston, Tex.

[21] Appl. No.: 923,998

[22] Filed: Oct. 28, 1986

[30] Foreign Application Priority Data

Nov. 27, 1985 [GB] United Kingdom ................ 8529199

[51] Int. Cl.$^4$ ........................ C07C 67/38; C07C 51/12
[52] U.S. Cl. ................................... 560/175; 502/153; 502/155; 502/162; 502/213; 560/176; 562/517; 562/578
[58] Field of Search ................ 560/175, 176; 562/517, 562/578; 502/153, 155, 162, 213

[56] References Cited

U.S. PATENT DOCUMENTS 3,448,140 6/1969 Gamlen et al. ...................... 560/34
4,474,978 10/1984 Drent et al. ........................... 560/24

FOREIGN PATENT DOCUMENTS 0121965 10/1984 European Pat. Off. .
5788149 11/1980 Japan .

*Primary Examiner*—Werren B. Lone
*Assistant Examiner*—Vera C. Clarke

[57] ABSTRACT

A process for the preparation of oxo-alkanedioic acids or diesters thereof by reacting an alkenoic acid or an ester thereof, at least one of the C atoms of the carbon carbon double bond carrying a H atom, with CO and $H_2$ in the presence of a catalytic system prepared by combining:

a. Pd and/or a Pd compound,
b. a compound containing an anion of an acid having a pKa of less than 2, except hydrohalogenic acid and carboxylic acids, and
c. a bidentate ligand

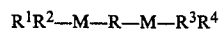
$$R^1R^2-M-R-M-R^3R^4$$

wherein M is P, As or Sb, R is a divalent organic bridging group having at least two C atoms in the bridge, and $R^1$, $R^2$, $R^3$ and $R^4$ are optionally substituted hydrocarbon groups.

19 Claims, No Drawings

PROCESS FOR THE PREPARATION OF OXO-ALKANEDIOIC ACIDS OR DIESTERS THEREOF

FIELD OF THE INVENTION

The invention relates to a process for the preparation of oxo-alkanedioic acids or diesters thereof.

BACKGROUND OF THE INVENTION

Diesters of oxo-alkanedioic acids can be used as an intermediate for the preparation of polyesters.

According to Japanese Patent Application 57 88,149 (1982), Application No. 80 162,878, dimethyl 4-oxo-heptanedioate (also referred to as "dimethyl γ-oxopimelate") can be prepared by reaction of carbon monoxide, water and methyl acrylate in the presence of organic phosphorus compounds having one or more than one trivalent phosphorus atom bound to the organic residue and of cobalt carbonyls. Disadvantages of this known process are that pure CO is used, being a gas which is usually obtained by isolation from synthesis gas containing carbon monoxide and hydrogen, and that carbon monoxide is applied at a relatively high partial pressure.

It is an object of the present invention to prepare oxo-alkanedioic acids or diesters thereof in good yield and with a very high selectivity, starting from a gas containing carbon monoxide and hydrogen and using relatively low partial pressure of carbon monoxide.

SUMMARY OF THE INVENTION

This invention provides a process for the preparation of oxoalkanedioic acids or diesters thereof, which process comprises reacting an alkenoic acid or an ester thereof, respectively, at least one of the carbon atoms of the carbon carbon double bond carrying a hydrogen atom, with carbon monoxide and hydrogen in the presence of a catalytic system prepared by combining:

(a) palladium and/or a palladium compound, (b) a compound containing an anion of an acid having a pKa of less than 2, provided it is neither a hydrohalogenic acid nor carboxylic acid and (c) a bidentate ligand of the general formula I $$R^1R^2-M-R-M-R^3R^4 \qquad (I)$$

wherein M represents a phosphorus, arsenic or antimony atom, R represents a divalent organic bridging group having at least two carbon atoms in the bridge, none of these carbon atoms carrying substituents that may cause steric hindrance and in which $R^1$, $R^2$, $R^3$ and $R^4$ represent identical or different optionally substituted hydrocarbon groups.

DESCRIPTION OF THE PREFERRED EMBODIMENTS

The anions used in the process according to the invention are preferably non-coordinating anions, by which is meant that little or no covalent interaction takes place between the palladium and the anion (cf. GB-A 2,058,074). Typical examples of such anions are $PF_6^-$, $SbF_6^-$, $BF_4^-$ and $ClO_4^-$.

Preferred anions are those of, for example, sulfonic acids and acids that can be formed, possibly in situ, by interacting a Lewis acid such as, for example $BF_3$, $AsF_5$, $SbF_5$, $PF_5$, $TaF_5$, or $NbF_5$ with a Broensted acid such as, for example, a hydrohalogenic acid, in particular HF, fluorosulfonic acid, phosphoric acid or sulfuric acid. Specific examples of acids of the latter type are $H_2SiF_6$, $HBF_4$, $HPF_6$ and $HSbF_6$. Examples of suitable sulfonic acids acids are fluorosulfonic acid and chlorosulfonic acid and the hereinafter specified sulfonic acids.

A preferred group of anions are anions of acids having the general formula II

(II)

in which X represents a sulfur or a chlorine atom and, if X represents a chlorine atom, $R^5$ represents an oxygen atom and, if X represents a sulfur atom, $R^5$ represents an OH group or an optionally substituted hydrocarbon group.

When the hereinbefore stated acids are used in the process according to the invention, the anions of the acids can be considered to be non-coordinating. The anions are preferably used in the form of the acids themselves, but under certain conditions it is also possible to use them in the form of salts, e.g. $AgBF_4$, $AgSbF_6$ or silver p-toluenesulfonate. The point is that it must be possible for the anion of the palladium compound to be exchanged with the anion of the salt.

In the acids having the general formula II, the optionally substituted hydrocarbon group represented by $R^5$ is preferably an alkyl, aryl, aralkyl or alkaryl group having 1-30, in particular 1-14, carbon atoms. The hydrocarbon group can, for example, be substituted with the halogen atoms, in particular fluorine atoms. Examples of suitable acids of the general formula II are perchloric acid, sulfuric acid, 2-hydroxypropane-2-sulfonic acid, p-toluenesulfonic acid and trifluoromethanesulfonic acid, the last two acids being the most preferred. The acid of the general formula II can also be an ion exchanger containing sulfonic acid groups, such as, for example, Amberlite 252 H ("Amberlite" is a trade name). In that case, the hydrocarbon group $R^5$ is a polymeric hydrocarbon group substituted with sulfonic acid groups, for example a polystyrene group.

The anion of the acid with a pKa of less than 2 is preferably present in the reaction mixture in a quantity in the range of from 0.01 to 150, in particular 0.1 to 100 and most preferably 1 to 50 equivalents per gram atom of palladium. The aforesaid pKa is measured in aqueous solution at 18° C.

The alkenoic acid will generally have less than 30 and preferably less than 12 carbon atoms per molecule. The acid may have a straight or branched chain of carbon atoms and the carbon carbon double bond may have any position in the chain of carbon atoms. At least one of the double bonded carbon atoms should carry a hydrogen atom. Very good results have been obtained with alkenoic acids having a carbon carbon double bond in the beta position with respect to the —C(O)OH group in the acid or the —C(O)O— group in the ester. Acrylic acid is the most preferred acid. Other examples of alkenoic acids are methacrylic acid, 2-butenoic acid, 2-pentenoic acid and 3-methyl-2-pentenoic acid. The alcohol from which the ester is derived may be a phenol, a cycloalkanol or, which is preferred, an alkanol, particularly an alkanol having less than 12 carbon atoms per molecule. Examples of suitable alkanols are haptanol, hexanol, pentanol, butanol, propanol, ethanol and, which is preferred, methanol. Very good results have been obtained with methyl acrylate.

The quantity of palladium compound is not critical. Preferably, quantities between $10^{-8}$ and $10^{-1}$ mol palladium compound per mol alkenoic acid or ester thereof are used. The molar ratio of alkenoic acid or ester thereof to carbon monoxide will as a rule be in the range of from 5:95 to 95:5, preferably from 1:5 to 5:1. The molar ratio of hydrogen to carbon monoxide is suitably in the range of from 1 to 5 to 5:1 and preferably from 1 to 2 to 2 to 1.

Both homogeneous and heterogeneous pallidum compounds can be used. Homogeneous systems are preferred. Suitable palladium compounds are salts of palladium with, for example nitric acid, sulfuric acid or alkanoic acids having not more than 12 carbon atoms per molecule. Salts of hydrohalogenic acids are theoretically also suitable, but have the drawback that the halogen ion may have a corrosive action. Palladium carboxylates are the catalyst compound preferably used, more preferably those having less than 12 carbon atoms per molecule, in particular palladium acetate. Palladium acetylacetonate is another example of a palladium compound that can be used. Palladium on carbon and palladium bonded to an ion exchanger, for example one containing sulfonic acid groups, are examples of suitable heterogeneous palladium compounds.

Where, in the bidentate ligand, it is said that substituents offering steric hindrance should be absent, this means that no substituents may be present that are able to hinder the formation of complex compounds having the general formula III

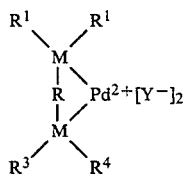

(III)

In that formula, Y represents a non-coordinating anion, while $Pd^{2+}$ can also be written as

in which the ligands $L_1$ and $L_2$ are weakly coordinated solvent ligands, e.g. acetonitrile, methanol, acetone, or acetylacetone, or correspond with those employed in the palladium compounds described in the preceding paragraph.

In the bidentate ligand, M preferably represents a phosphorus atom. Hydrocarbon groups $R^1$, $R^2$, $R^3$ and $R^4$ will generally contain 2 to 18 carbon atoms, preferably 6 to 14 carbon atoms. Aryl grous are the most suitable, in particular the phenyl group. Preferred bridging groups —R— are those having the formula

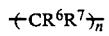

in which $R^6$ and $R^7$ are hydrocarbon atoms or optionally substituted hydrocarbon groups offering no steric hindrance and n is an integer of at least two, preferably not more than 5, and most preferably 2, 3 or 4. Substituents $R^6$ and $R^7$ are preferably hydrogen atoms. The bridging groups R may also make part of a cyclic structure, e.g. an aromatic or cycloaliphatic group, the carbon to carbon bond or bonds in the bridge may be saturated or unsaturated and in the bridge or in the cyclic or non-cyclic groups attached to the bridge one or more hetero atoms, e.g. sulfur, oxygen, iron or nitrogen, may have been substituted for carbon atoms, other than the two carbon atoms which must be present in the bridge linking both atoms M.

Examples of suitable bidentate ligands are
1,3-di(diphenylphosphino)propane,
1,4-di(diphenylphosphino)butane,
2,3-dimethyl-1,4-di(diphenylphosphino)butane,
1,5-di(methylphenylphosphino)pentane,
1,4-di(dicyclohexylphosphino)butane,
1,5-di(dinaphthylphosphino)pentane,
1,3-di(di-p-tolylphosphino)propane,
1,4-di(di-p-methoxyphenylphosphino)butane,
1,2-di(diphenylphosphino)ethene,
2,3-di(diphenylphosphino)-2-butene,
1,3-di(diphenylphosphino)-2-oxopropane,
2-methyl-2-(methyldiphenylphosphino)-1,3-di(diphenylphosphino)propane,
O,O'-di(diphenylphosphino)biphenyl,
1,2-di(diphenylphosphino)benzene,
2,3-di(diphenylphosphino)naphthalene,
1,2-di(diphenylphosphino)cyclohexane,
2,2-dimethyl-4,5-di(diphenylphosphino)dioxolane and

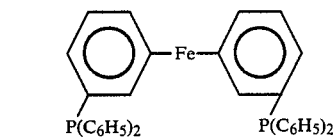

Very good results have been obtained with 1,3-di(diphenylphosphino)propane.

The bidentate ligand can be used in quantities, relative to the palladium compound, that can range within wide limits, e.g. from 0.1 to 10 mol per mol palladium compound. Preferred quantities range from 0.33 to 3 mol per mol.

If desired, one or more monodentate ligands can also be used in the preparation of the catalyst. Suitable monodentate ligands are in particular triarylphosphines, such as triphenylphosphine and trinaphthylphosphine. The use of an excees of monodentate ligand in relation to palladium is recommended. Preferred quantities range from 10:1 to 60:1 in relation to palladium.

The carbon monoxide and the hydrogen can be used in pure form or diluted with an inert gas such as nitrogen, noble gases or carbon dioxide in the process according to the invention.

The process of this invention is preferbly carried out at a temperature in the range of from 20° C. to 200° C., in particular 50 to 150° C., and a total pressure in the range of from 2 to 100, in particular 20 to 75 bar. It can be carried out batchwise, continuously or semi-continuously. In general, reaction times between 1 and 20 hours appear to be adequate.

The process according to the invention is suitably carried out in the presence of an aprotic solvent. Examples of such solvents are hydrocarbons, such as hexane, octane, benzene, toluene, the three xylenes, ethylbenzene, cumene and cyclohexane; halogenated hydrocarbons, such as chloroform, 1,2-dichloroethane, perfluoroalkanes, chlorobenzene and the three dichlorobenzenes; sulfones such as diethyl sulfone, diisopropyl sulfone and tetrahydrothiophene 1,1-dioxide (also referred to as "sulfolane"); N,N-dialkyl-substituted amides such as N,N-dimethylformamide and N-methylpyrrolidone; esters such as methylbenzoate, ethyl acetate and amyl acetate; ethers such as diethyl ether, 3,6-dioxaoctane, methyl tert.-butylether, tetrahydrofuran, diisopropyl ether, dioxane, 2,5,8-trioxanonane (also referred to as "diglyme"), diphenyl ether and anisole.

The oxo-alkanedioic acids or diesters thereof may be isolated from the reaction mixture in any suitable manner, for example by means of distillation, obtaining a distillate fraction containing the acid or diester, and a bottom fraction containing the catalytic system. Suitably, an aprotic solvent is chosen that substantially remains in the bottom fraction. Preferably, at least a portion of the bottom fraction containing aprotic solvent and catalytic system is re-used in the process according to the invention.

The following example further illustrates the invention and is not to be construed as limiting the invention. The selectivity to a certain compound, expressed in a percentage, is defined herein as 100 × a/b, in which "a" is the amount of starting compound that has been converted into that certain compound and "b" is the total amount of starting compound that has been converted.

EXAMPLE

A magnetically stirred 300-ml autoclave was charged with methyl acrylate (20 ml), diglyme (50 ml), palladium(II) acetate (0.1 mmol), 1,3-di(diphenylphosphino)propane (0.10 mmol) and p-toluenesulfonic acid (2 mmol). The autoclave was flushed with carbon monoxide, charged with carbon monoxide until a partial pressure thereof of 20 bar was reached, charged with hydrogen until a partial pressure thereof of 20 bar was reached, sealed and heated at 135° C. for 5 h. Analysis by means of gas-liquid mass spectroscopy showed that the conversion of methyl acrylate was 45%, with a selectivity to dimethyl 4-oxo-heptanedioate of more than 90%.

I claim as my invention:

1. A process for the preparation of oxo-alkanedioic acids or diesters thereof, which process comprises reacting an alkenoic acid or an ester thereof having at least one carbon-carbon double bond, respectively, at least one of the carbon atoms of the carbon-carbon double bond carrying a hydrogen atom, with carbon monoxide and hydrogen in the presence of a catalytic system prepared by combining:
(a) palladium and/or a palladium compound,
(b) a compound containing an anion of an acid having a pKa of less than 2, provided it is neither a hydrohalogenic acid nor carboxylic acid and
(c) a bidentate ligand of the formula I $$R^1R^2-M-R-M-R^3R^4 \quad (I)$$

wherein M represents a phosphorus, arsenic or antimony atom, R represents a divalent organic bridging group having at least two carbon atoms in the bridge, none of these carbon atoms carrying substituents that may cause steric hindrance and in which $R^1$, $R^2$, $R^3$ and $R^4$ represent identical or different optionally substituted hydrocarbon groups.

2. The process of claim 1 wherein as anion, a non-coordinating anion is used.

3. The process of claim 2 wherein an anion of a sulfonic acid or of an acid that can be formed by interacting a Lewis acid with a Broensted acid is used.

4. The process of claim 1 wherein an anion of an acid having the formula II

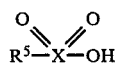

(II)

wherein X represents a sulfur or a chlorine atom and, if X represents a chlorine atom, $R^5$ represents an oxygen atom and, if X represents a sulfur atom, $R^5$ represents an OH group or an optionally substitued hydrocarbon group is used.

5. The process of claim 4 wherein the hydrocarbon group $R^5$ is an alkyl, aryl, aralkyl or alkaryl group with 1-30 carbon atoms.

6. The process of claim 4 wherein an anion of p-toluenesulfonic acid or trifluoromethanesulfonic acid is used.

7. The process of claim 1 wherein group —R— represents a group

in which $R^6$ and $R^7$ represent hydrogen atoms or optionally substituted hydrocarbon groups offering no steric hindrance and n is an integer of at least 2.

8. The process of claim 7 wherein n is an integer of not more than 5.

9. The process of claim 1 wherein the hydrocarbon groups $R^1$, $R^2$, $R^3$ and $R^4$ are optionally substituted aryl groups with 6-14 carbon atoms.

10. The process of claim 9 wherein the aryl groups are optionally substituted phenyl groups.

11. The process of claim 10 wherein the bidentate ligand is 1,3-di(diphenylphosphino)propane.

12. The process of claim 1 wherein 0.33-3 mol bidentate ligand per gram atom palladium is used.

13. The process of claim 1 wherein the ester of the alkenoic acid is an alkyl ester.

14. The process of claim 13 wherein the alkenoic acid and the alkyl group of the alkyl ester have less than 12 carbon atoms.

15. The process of claim 14 wherein the alkenoic acid is acrylic acid.

16. The process of claim 14 wherein the ester is methyl acrylate.

17. The process of claim 1 wherein said process is carried out at a temperature in the range of from 20° C. to 200° C.

18. The process of claim 1 wherein said process is carried out at a pressure in the range of from 2 to 100 bar.

19. The process of claim 1 wherein said process is carried out in the presence of an aprotic solvent.

* * * * *